United States Patent [19]
Bauer et al.

[11] Patent Number: 4,841,948
[45] Date of Patent: Jun. 27, 1989

[54] CONCAVE BASE TISSUE EXPANDER

[75] Inventors: Bruce S. Bauer, Lincolnwood, Ill.; William R. Dubrul; Tor E. Allen, both of Santa Barbara, Calif.

[73] Assignee: McGhan Medical Corporation, Santa Barbara, Calif.

[21] Appl. No.: 105,001

[22] Filed: Oct. 6, 1987

[51] Int. Cl.⁴ .................... A61B 19/00; A61F 2/02
[52] U.S. Cl. ........................ 128/897; 623/11
[58] Field of Search .................... 623/8, 7, 11, 12; 128/1 R, 344

[56] References Cited
U.S. PATENT DOCUMENTS

| | | | |
|---|---|---|---|
| 4,217,889 | 8/1980 | Radovan et al. | 128/1 R |
| 4,615,704 | 10/1986 | Frisch | 128/1 R X |
| 4,636,213 | 1/1987 | Pakiam | 623/8 |
| 4,666,447 | 5/1987 | Smith et al. | 128/1 R X |
| 4,685,447 | 8/1987 | Iversen et al. | 128/1 R |
| 4,719,918 | 1/1988 | Bonomo et al. | 128/1 R X |

Primary Examiner—Ronald L. Frinks
Attorney, Agent, or Firm—Michael G. Petit

[57] ABSTRACT

A tissue expander device comprising a thin expandable cover and a concave base is disclosed. Together, the cover and the base form an envelope with a cambered interior chamber concave on the base and convex on the cover. The volume of the envelope is adjusted by introducing fluid into the chamber. As the device is inflated, the radius of curvature of the cambered base is gradually increased until the base becomes substantially planar when the device is fully inflated. Since the concave base becomes planar when the device is fully inflated, the surface of the device contacting the thin overlying skin is smooth and continuous thus reducing erosion of the skin flap by the edge of the base.

3 Claims, 1 Drawing Sheet

CONCAVE BASE TISSUE EXPANDER

BACKGROUND OF THE INVENTION

Tissue expansion devices have been used by plastic surgeons for over thirty years for the generation of skin flaps in reconstructive surgery. Skin expansion is commonly observed, for example, in pregnant women. For the overlying skin to remain healthy, the expansion must take place gradually as in the case of the developing fetus. Additionally, the underlying pressure on the skin must be distributed uniformly to prevent necrosis of the thin overlying tissue. These considerations have guided the development of the tissue expansion devices currently in use.

It is particularly desirable to generate a donor skin flap on a portion of the body contiguous with the recipient area. In this way, skin texture and abundance of hair in the grafted area can be made to more or less blend with the surrounding skin giving a more esthetically pleasing result. To accomplish this, the surgeon makes a pocket under the skin and subcutaneous tissue adjacent to the area to be grafted. A tissue expander is placed in the pocket and gradually inflated over a period of weeks or months until the device is fully inflated. Since the base of most tissue expanders is thicker and less flexible than the cover, the envelope presses upward during expansion stretching the overlying skin. As the skin stretches, it becomes thinner and more vulnerable to trauma. In particular, if the underlying pressure on such distended skin is excessive, circulation may be impaired with resulting necrosis and death of cells.

Due to the tension on the periphery of the base of conventional tissue expanders caused by the upward pull of the expanded flexible cover, the edges of the base can curl up when the device is fully expanded or over-expanded. If the base curls up, it can cause excessive pressure on the thin overlying skin which can result in necrosis and erosion. It is the object of the present invention to provide a tissue expander with a base that protects the overlying tissue against damage associated with base pressure observed with fully inflated or over-inflated current art devices.

SUMMARY OF THE INVENTION

It is the object of the present invention to provide a tissue expander device which, when fully inflated, reduces or eliminates damage to the overlying skin due to excessive pressure caused by curling of the base up into the thin overlying skin. The feature of the present invention which accomplishes this is the concave base. The operation of this feature can be best understood by reference to the following description taken together with the accompanying drawings.

BRIEF DESCRIPTION OF THE DRAWINGS

FIG. 3 (b) is a corresponding cross-sectional view of FIG. 3 (a) for a conventional flat based tissue expander.

FIG. 4 (b) is the cross-sectional view of FIG. 3 (b) when the conventional flat-based tissue expander is fully inflated.

DESCRIPTION OF THE PREFERRED EMBODIMENT

Figure 1:
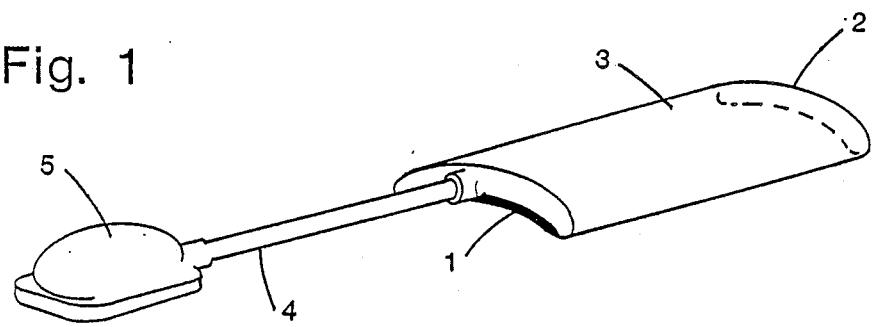
FIG. 1 is a schematic perspective view of the tissue expander of the present invention before inflation.

The following specification taken together with the drawings sets forth the preferred embodiment of the present invention. The embodiment of the invention disclosed herein is the best mode contemplated by the inventors for carrying out their invention in a commercial environment. It should be understood that various modifications can be accomplished within the scope of the present invention.

The tissue expander device (3) for surgical implantation beneath the skin and subcutaneous layer includes a flexible concave base (1), a thin expandable cover (2) of biocompatible elastic material attached to the base to form a continuous fluid-tight envelope with a chamber therein, and an injection reservoir (5) in fluid communication with the chamber comprising means for admitting fluid to the chamber with a hypodermic needle without puncturing the cover or base and means for substantially leak-proof sealing of the injection reservoir after the needle is withdrawn. The injection reservoir (5) is connected to the envelope by means of a fill tube (4) and includes an outer wall having a substantially dome-shaped sealing member affixed to the outer wall with the sealing member being self-sealing to punctures by the hypodermic needle.

Turning now to FIG. 1, the inflatable cover (2) is a thin expandable membrane of medical grade silicone elastomer approximately 0.015" thick. The cover can be made by dipping a formed mandrel (not shown) into a silicone dispersion to the correct thickness, curing and removing from the mandrel. The base (1) of thickness approximately 0.060" is cut to shape from raw silicone and inserted into the interior of the cover through the hole (not shown) previously cut to remove the cover from the mandrel. The base is positioned within the cover, and vulcanized to the cover by pressing over a substantially cylindrical heated platen of correct curvature (not shown) to effect the desired concavity. The fill tube (4) and injection reservoir (5) may be affixed to the cover (2) either by cementing or during the dipping process by insertion of the fill tube (4) into a receiving hole in the mandrel prior to dipping.

Figure 2:
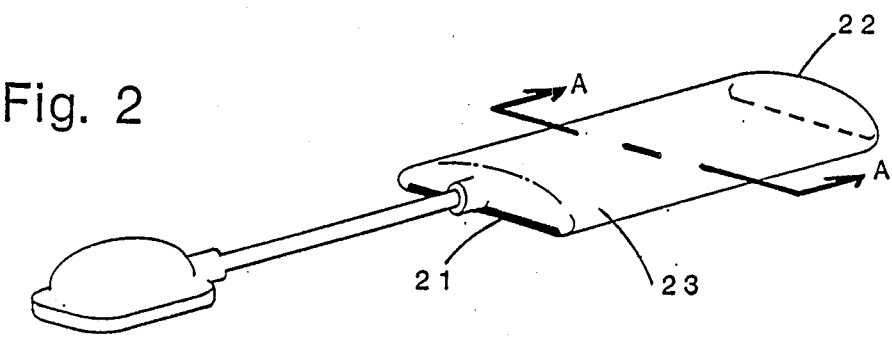
FIG. 2 is a schematic perspective view of the tissue expander of the present invention when fully inflated.

The fully expanded device is shown in FIG. 2. Since the equilibrium position of the base is concave downward, as the device is inflated there is tension created in the base (21) which tends to pull the edges of the base downward to resist the upward pull of the expanded cover (22). This opposing force exerted by the tension created in the base substantially prevents the edges of the base from turning upward during inflation. Since the base (21) and the cover (22) are of different thickness and stiffness, a ridge (23) is created at the periphery of the base. Owing to the concave shape of the base, the ridge is substantially prevented from turning upward to press on the thin overlying tissue. The flexible concave base (21) becomes substantially planar when the tissue expander device is fully inflated as shown in FIG. 2.

Figure 3A:
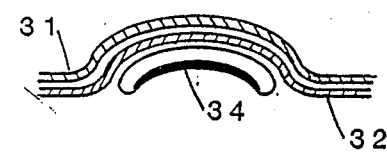
FIG. 3 (a) is a cross-sectional view along A—A' (FIG. 2) of the implanted tissue expander device of the present invention prior to inflation.
Figure 3B:
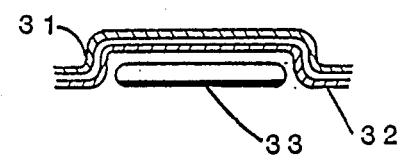
Figure 4A:
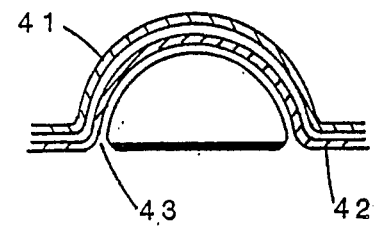
FIG. 4 (a) is the cross-sectional view of FIG. 3 (a) when the tissue expander is fully inflated.
Figure 4B:
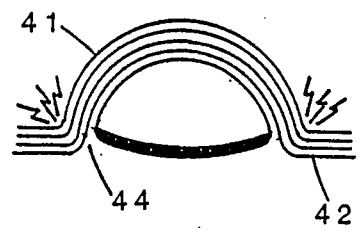

The effect of the concave base will be appreciated by turning now to FIGS. 3 and 4. FIG. 3 (a) shows the device (33) of the present invention in position under the skin (31) and subcutaneous tissue (32) prior to inflation. FIG. 3 (b) depicts a flat-based device (34) of the current art in a corresponding position. FIG. 4 (a)

shows the implanted device of the present invention fully inflated. The ridge at the border of the base (43) is constrained from turning upward whereas the flat-based device (FIG. 4b) will present a raised ridge (44) to the thin overlying skin (41) and subcutaneous tissue (42) with resulting trauma.

This invention is not be limited by the embodiments shown in the drawings and described in the specification which is given by way of example and not of limitations, but only in accordance with the scope of the appended claims.

What we claim is:

1. A tissue expander device for surgical implantation beneath the skin and subcutaneous layer, the tissue expander comprising:

(a) a concave base;

(b) a thin expandable cover comprising biocompatible elastic material attached to the base to form a continuous fluid-tight envelope with a chamber therein;

(c) an injection reservoir in fluid communication with said chamber comprising means for admitting fluid to the chamber with a hypodermic needle without puncturing the cover or the base and means for substantially leak-proof sealing of the injection reservoir after the needle is withdrawn therefrom.

2. A device according to claim 1 wherein said concave base is flexible and becomes substantially planar when the device is fully inflated.

3. The device of claim 2 wherein the base comprises a concave sheet of biocompatible material having substantially greater thickness than the cover.

* * * * *